(12) United States Patent
 Kaiser et al.

(10) Patent No.: US 8,180,428 B2
(45) Date of Patent: May 15, 2012

(54) METHODS AND SYSTEMS FOR USE IN SELECTING CARDIAC PACING SITES

(75) Inventors: Daniel R. Kaiser, St. Paul, MN (US); Michael R. Neidert, Salthill (IE); Nicholas David Skadsberg, Blaine, MN (US); Kenneth C. Gardeski, Plymouth, MN (US); Lawrence J. Mulligan, Andover, MN (US); James F. Kelley, Coon Rapids, MN (US); Michael B. Shelton, Minneapolis, MN (US); Trent M. Fischer, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 511 days.

(21) Appl. No.: 12/421,176

(22) Filed: Apr. 9, 2009

(65) Prior Publication Data
US 2009/0198298 A1    Aug. 6, 2009

Related U.S. Application Data

(63) Continuation-in-part of application No. 12/245,570, filed on Oct. 3, 2008.

(60) Provisional application No. 60/977,098, filed on Oct. 3, 2007.

(51) Int. Cl.
*A61B 5/00* (2006.01)

(52) U.S. Cl. ........ 600/411; 600/427; 600/429; 600/374; 600/407; 600/424; 600/508; 600/536; 606/130; 607/7; 607/9; 607/18

(58) Field of Classification Search .................. 600/508, 600/527, 536, 407, 410, 411, 425, 427, 424, 600/429, 374; 606/130; 378/4; 607/17, 607/7, 9, 18
See application file for complete search history.

(56) References Cited

U.S. PATENT DOCUMENTS

| 4,173,228 | A | 11/1979 | Van Steenwyk et al. |
|---|---|---|---|
| 5,549,650 | A | 8/1996 | Bornzin et al. |
| 5,549,652 | A | 8/1996 | McClure et al. |
| 5,592,939 | A | 1/1997 | Martinelli |
| 5,697,377 | A | 12/1997 | Wittkampf |

(Continued)

OTHER PUBLICATIONS

Lieberman et al., "Ventricular Pacing Lead Location Alters Systemic Hemodynamics and Left Ventricular Function in Patients With and Without Reduced Ejection Fraction," *J.Am. Coll. Cardiol.*, 2006; 48(8):1634-1641. Originally published online Sep. 26, 2006.

(Continued)

*Primary Examiner* — Brian Casler
*Assistant Examiner* — Amanda Lauritzen
(74) *Attorney, Agent, or Firm* — Carol F. Barry; Reed A. Duthler (57) ABSTRACT

A method and system for use in selecting a cardiac pacing site includes sensors for tracking wall motion (e.g., sensors coupled to the right and left ventricular heart wall). The wall motion of one or more non-paced cardiac cycles is compared to the wall motion of one or more paced cardiac cycles to determine the effectiveness of one or more pacing sites. For example, image data may be generated to notify the user as to the effectiveness of the one or more pacing sites.

30 Claims, 7 Drawing Sheets

U.S. PATENT DOCUMENTS

| | | | |
|---|---|---|---|
| 5,727,553 | A | 3/1998 | Saad |
| 5,738,096 | A | 4/1998 | Ben-Haim |
| 5,913,820 | A | 6/1999 | Bladen et al. |
| 5,983,126 | A | 11/1999 | Wittkampf |
| 6,002,963 | A | 12/1999 | Mouchawar et al. |
| 6,009,349 | A | 12/1999 | Mouchawar et al. |
| 6,066,094 | A | 5/2000 | Ben Haim |
| 6,104,944 | A | 8/2000 | Martinelli |
| 6,285,898 | B1 | 9/2001 | Ben-Haim |
| 6,368,285 | B1 | 4/2002 | Osadchy et al. |
| 6,411,849 | B1 * | 6/2002 | Shankar et al. ............. 607/19 |
| 6,807,439 | B2 | 10/2004 | Edwards et al. |
| 6,892,090 | B2 | 5/2005 | Verard et al. |
| 6,915,149 | B2 * | 7/2005 | Ben-Haim ............. 600/374 |
| 7,092,759 | B2 * | 8/2006 | Nehls et al. ............. 607/19 |
| 7,294,334 | B1 * | 11/2007 | Michal et al. ............. 424/93.7 |
| 7,610,088 | B2 * | 10/2009 | Chinchoy ............. 607/17 |
| 7,676,268 | B2 | 3/2010 | Hettrick et al. |
| 2003/0105495 | A1 | 6/2003 | Yu et al. |
| 2004/0097806 | A1 | 5/2004 | Hunter et al. |
| 2005/0099290 | A1 | 5/2005 | Govari |
| 2006/0178586 | A1 | 8/2006 | Dobak, III |
| 2006/0235289 | A1 * | 10/2006 | Wesselink et al. ............. 600/407 |
| 2007/0055124 | A1 | 3/2007 | Viswanathan et al. |
| 2007/0164900 | A1 | 7/2007 | Schneider et al. |
| 2008/0058656 | A1 | 3/2008 | Costello et al. |
| 2008/0132800 | A1 | 6/2008 | Hettrick et al. |
| 2008/0242976 | A1 * | 10/2008 | Robertson et al. ............. 600/425 |
| 2008/0285909 | A1 | 11/2008 | Younge et al. |
| 2009/0125078 | A1 * | 5/2009 | Kaiser et al. ............. 607/27 |
| 2010/0049063 | A1 * | 2/2010 | Dobak, III ............. 600/508 |
| 2010/0280366 | A1 * | 11/2010 | Arne et al. ............. 600/425 |
| 2011/0118803 | A1 | 5/2011 | Hou et al. |

OTHER PUBLICATIONS

Salgo, "Clinical benefits of QLAB software for advanced 2D and 3D echo quantification," Phillips Medical Systems, Eindhoven, NL, 2006. Available on the Internet at: <URL:http://incenter.medical.philips.com/doclib/fetch/2000/4504/577242/577260/593280/593431/Clinical_benefits_of_QLAB_software_for_advanced_2D_and_3D_echo_quantification_(outside_U.S.)?nodeid=1827474&vernum=1>; 16 pgs.

Wittkampf et al., "LocaLisa: New Technique for Real-Time 3-Dimensional Localization of Regular Intracardiac Electrodes," *Circulation*, 1999; 99:1312-1317.

Proteus, "Electric Tomography (ET)—A Novel Method for Assessing Myocardial Motion and Cardiac Performance", by George Savage MD, et al., Heart Rhythm Society, May 9-12, 2007, Denver, Colorado.

* cited by examiner

METHODS AND SYSTEMS FOR USE IN SELECTING CARDIAC PACING SITES

CROSS-REFERENCE TO RELATED APPLICATION

The present application is a continuation-in-part application of U.S. patent application Ser. No. 12/245,570 filed Oct. 3, 2008, which claims the benefit of U.S. Provisional Patent Application Ser. No. 60/977,098 filed on Oct. 3, 2007, both of which are incorporated herein by reference in their entirety.

TECHNICAL FIELD

The present disclosure pertains to cardiac pacing and more particularly to methods and systems for use in selecting cardiac pacing sites.

BACKGROUND

In recent years cardiac resynchronization therapy (CRT) for patients suffering from chronic heart failure has been shown to increase exercise capacity and a quality of life for these patients. CRT, for example, may be administered via bi-ventricular pacing delivered via implanted medical electrodes, and the outcome of the therapy is often highly dependent upon selecting, and then successfully implanting the electrodes at appropriate pacing sites. In this context, as well as others, for example, such as physiological or dual chamber pacing, alternate pacing sites may be evaluated via measurement of the electrical and/or mechanical response of the heart to the pacing. For example, many assert that pacing is most effective if mechanical synchrony between the right and left ventricle can be maintained or re-established. Thus, physicians may prefer to assess the mechanical, or hemodynamic, response of the heart to pacing at various implant sites before selecting one or more locations for chronic pacing. Tissue Doppler Imaging (TDI) is one of several methods currently employed, for example, to assess the mechanical response of a heart to pacing.

BRIEF DESCRIPTION OF THE DRAWINGS

The following drawings are illustrative of particular embodiments of the present disclosure and therefore do not limit the scope of the disclosure. The drawings are not to scale (unless so stated) and are intended for use in conjunction with the explanations in the following detailed description.

Embodiments of the present disclosure will hereinafter be described in conjunction with the appended drawings, wherein like numerals denote like elements.

DETAILED DESCRIPTION

The following detailed description is exemplary in nature and is not intended to limit the scope, applicability, or configuration of the disclosure in any way. Rather, the following description provides practical illustrations for implementing exemplary embodiments of the present disclosure. Various constructions, materials, dimensions, and manufacturing processes may be suitable for making and/or using one or more embodiments described herein.

In one or more embodiments, a system, method, or computer readable medium (e.g., including one or more programs including one or more instructions executable by a computer) described herein may simplify intra-operative monitoring of the mechanical response of the heart to pacing at various sites. For example, such monitoring may be used to facilitate selection of effective pacing sites (e.g., left ventricular, right ventricular, or bi-ventricular pacing sites, and further, endocardial and/or epicardial sites).

In parallel with the development of CRT, techniques employing image-guided surgical navigation technology have been developed for the navigation of catheters, or leads, within the heart to assist in the placement of pacing electrodes. For example, in one or more exemplary embodiments, image-guided navigation systems described in co-pending and commonly assigned U.S. Patent Application Publication No. 2004/0097806 entitled NAVIGATION SYSTEM FOR CARDIAC THERAPIES, which is hereby incorporated by reference in its entirety, may be employed to carry out one or more methods described herein, or portions thereof, including being used to monitor cardiac wall motion in response to pacing at various sites and/or when the heart is not being paced (e.g., may be employed with one or more modifications, such as with use of one or more algorithms to assist in collecting data with regard to wall motion and/or visualization of data representative of wall motion of the heart, either when the heart is being paced and/or when the heart is not being paced).

Figure 1:
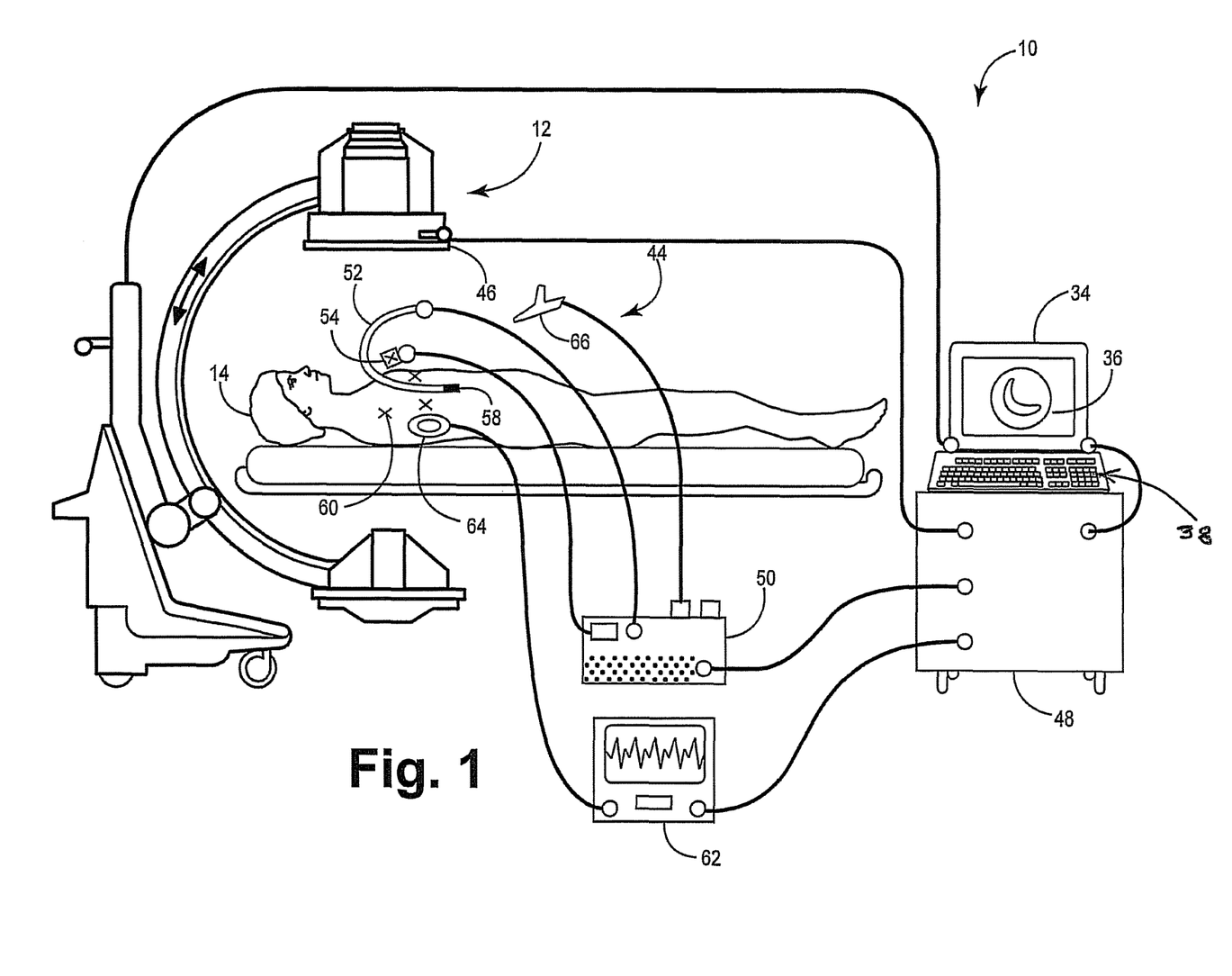
FIG. 1 is a diagram of an exemplary system for carrying out one or more exemplary methods of the present disclosure.

FIG. 1 is a diagram of an image guided catheter navigation system 10 that may be used to navigate catheters, or leads, within the body. For example, the principles described herein are applicable to all types of medical electrical leads. For example, the disclosure applies to cardiovascular leads (e.g., high voltage leads, low voltage leads, etc.), neurological leads, and/or are applicable to other suitable applications in which medical leads are employed. Further, a lead may be adapted to carry out various functions, for example, in facilitating delivery of pacing to a target site and/or sensing wall location, and can, thus, in various embodiments, take the form of a catheter, a pacing lead, any other like device, etc. This same system 10 is further configured to provide wall motion data representative of heart wall motion (e.g., both when pacing is applied to the heart and also when no pacing is applied).

FIG. 1 illustrates system 10 which generally includes an imaging device 12, an electromagnetic navigation or tracking system 44, a gating device (e.g., an electrocardiograph) 62, and a controller or work station 34, which may receive input from each of the aforementioned devices. For example, two dimensional fluoroscopic images taken by the imaging device 12 may be captured and stored by the imaging device 12. Such images may be forwarded from the imaging device 12 to controller or work station 34 (e.g., a computer or computing device) having and/or associated with a display 36 and a user interface 38.

The work station 34 provides facilities, for example, to display images on the display 36, saving and or storing data (e.g., wall motion data), digitally manipulate data (e.g., wall motion data) such as that to be displayed, provide notification to a user as described herein, or printing a hard copy of received images. The user interface 38, which may be a keyboard, mouse, touch pen, touch screen or other suitable device, allows a physician or other user to provide inputs to control the imaging device 12 and/or other portions of system 10, adjust the display settings of the display 36, select one or more images to be displayed, and/or execute one or more programs to perform one or more functions as described herein.

It will be recognized that while a fluoroscopic C-arm imaging device 12 is shown in FIG. 1, any other alternative imaging modality may also be used. For example, isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), 2D, 3D or 4D ultrasound, or intraoperative CT or MRI may also be used to acquire pre-operative or real-time images or image data of the patient 14. The images may also be obtained and displayed in two or three dimensions. In more advanced forms, four-dimensional surface rendering of the heart or other regions of the body may also be achieved by incorporating heart data or other soft tissue data from an atlas map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data to be used to confidently reach target sights within the heart or other areas of interest. Further, for example, it is further noted by acquiring images in more than one plane, an icon representing the location of a catheter or other instrument, introduced and advanced in the patient 14, may be superimposed in more than one view on display 36 allowing simulated bi-plane or even multi-plane views, including two and three-dimensional views.

In one or more embodiments, as shown in FIG. 1, the electromagnetic navigation or tracking system 44 of the system 10 may include a transmitter coil array 46, a coil array controller 48 (which may or may not be incorporated in work station 34 or provided as a separate controller), a navigation probe interface 50, an electromagnetic catheter 52 and a dynamic reference frame 54. It should further be noted that the entire tracking system 44 or parts of the tracking system 44 may be incorporated into the imaging device 12, including the work station 34.

The transmitter coil array 46 is shown attached to the imaging device 12. However, it should be noted that the transmitter coil array 46 may also be positioned at any other location as well. For example, the transmitter coil array 46 may be positioned at the x-ray source 18, within the OR table positioned below the patient 14, on siderails associated with the table 56, or positioned on the patient 14 in proximity to the region being navigated, such as on the patient's chest. The transmitter coil array 46 includes a plurality of coils that are each operable to generate distinct electromagnetic fields into the navigation region of the patient 14, which is sometimes referred to as patient space.

The transmitter coil array 46 is controlled or driven by the coil array controller 48. For example, the coil array controller 48 may drive each coil in the transmitter coil array 46 in a time division multiplex and/or a frequency division multiplex manner. In this regard, each coil may be driven separately at a distinct time or all of the coils may be driven simultaneously with each being driven by a different frequency. Upon driving the coils in the transmitter coil array 46 with the coil array controller 48, electromagnetic fields are generated within the patient 14 in the region (e.g., volume) where the medical procedure is being performed, which is again sometimes referred to as the patient space. The electromagnetic fields generated in the patient space induce currents in sensors 58 (e.g., sensing coils) positioned in the catheter 52 (or sensors positioned in each of multiple leads).

These induced signals from the catheter 52 are delivered to the navigation probe interface 50 and subsequently forwarded to the coil array controller 48. The navigation probe interface 50 provides all the necessary electrical isolation for the navigation system 10. The navigation probe interface 50 also includes amplifiers, filters and buffers required to directly interface with the sensors 58 in catheter 52. Alternatively, the catheter 52 may employ a wireless communications channel as opposed to being coupled directly to the navigation probe interface 50.

The catheter 52, may be equipped with at least one, and generally multiple sensors 58 (e.g., electromagnetic sensing coils). The catheter 52 is also generally a steerable catheter that includes a handle at a proximal end and the multiple location sensors 58 fixed to the catheter body and spaced axially from one another along the distal segment of the catheter 52. The sensors 58 may be formed as electromagnetic receiver coils such that the electromagnetic field generated by the transmitter coil array 46 induces current in the electromagnetic receiver coils or sensors 58. The catheter 52 may also be equipped with one or more sensors, which are operable to sense various physiological signals. For example, the catheter 52 may be provided with electrodes for sensing myopotentials or action potentials. An absolute pressure sensor may also be included, as well as other electrode sensors or pacing electrodes. The catheter 52 may also be provided with an open lumen, further discussed herein, to allow the delivery of a medical device or pharmaceutical agent. For example, the catheter 52 may be used as a guide catheter for deploying a medical lead, such as a cardiac lead for use in cardiac pacing and/or defibrillation or tissue ablation.

In an alternate embodiment, the electromagnetic sources or generators may be located within the catheter 52 and one or more receiver coils may be provided externally to the patient 14 forming a receiver coil array similar to the transmitter coil array 46. In this regard, the sensor coils 58 would generate electromagnetic fields, which would be received by the receiving coils in the receiving coil array similar to the transmitter coil array 46. Other types of localization sensors may also be used, which may include an emitter, which emits energy, such as light, sound, or electromagnetic radiation, and a receiver that detects the energy at a position away from the emitter. This change in energy, from the emitter to the receiver, is used to determine the location of the receiver relative to the emitter. An additional representative alternate localization and tracking system is set forth in U.S. Pat. No. 5,983,126, entitled "Catheter Location System and Method," issued Nov. 9, 1999, which is hereby incorporated by reference. Alternatively, the localization system may be a hybrid system that includes components from various systems. As used herein, the term sensor refers not only to electromagnetic receiver coils but also to any other sensor (e.g., electromagnetic emitter coil) which when provided as part of a lead as described herein is used to provide tracking and/or monitoring of the location of the sensor, such as when used to monitor wall motion.

The dynamic reference frame 54 of the electromagnetic tracking system 44 is also coupled to the navigation probe interface 50 to forward the information to the coil array controller 48. The dynamic reference frame 54 may be a small magnetic field detector that is designed to be fixed to the patient 14 adjacent to the region being navigated so that any movement of the patient 14 is detected as relative motion between the transmitter coil array 46 and the dynamic reference frame 54. This relative motion is forwarded to the coil array controller 48, which updates registration correlation and maintains accurate navigation. For example, the dynamic reference frame 54 can be configured as a pair of orthogonally oriented coils, each having the same center or may be configured in any other non-coaxial coil configuration. The dynamic reference frame 54 may be affixed externally to the patient 14, adjacent to the region of navigation, such as on the patient's chest, as shown in FIG. 1 or on the patient's back. Alternatively, the dynamic reference frame 54 may be internally attached, for example, to the wall of the patient's heart or other soft tissue using a temporary lead that is attached directly to the heart. Further, for example, multiple dynamic reference frames 54 may also be employed.

The catheter and navigation system 10 further includes a gating device 62 (e.g., an ECG or electrocardiogram 62), which may be attached to the patient 14, via skin electrodes 64, and in communication with the coil array controller 48. Respiration and cardiac motion can cause movement of cardiac structures relative to the catheter 54, even when the catheter 54 has not been moved. Therefore, localization data may be acquired on a time-gated basis triggered by a physiological signal. For example, the ECG or EGM signal may be acquired from the skin electrodes 64 or from a sensing electrode included on the catheter 54 or from a separate reference probe. A characteristic of this signal, such as an R-wave peak or P-wave peak associated with ventricular or atrial depolarization, respectively, may be used as a triggering event for the coil array controller 48 to drive the coils in the transmitter coil array 46. This triggering event may also be used to gate or trigger image acquisition during the imaging phase with the imaging device 12. By time-gating the image data and/or the navigation data, the location of the catheter 52 relative to the heart at the same point in the cardiac cycle may be displayed on the display 36.

Briefly, for example, the navigation system 10 may operate as follows. The navigation system 10 may create a translation map between all points in the radiological image generated from the imaging device 12 and the corresponding points in the patient's anatomy in patient space. After this map is established, whenever a tracked instrument, such as the catheter 52 or pointing device is used, the work station 34 in combination with the coil array controller 48 and a controller of the imaging device 12 uses the translation map to identify the corresponding point on the pre-acquired image, which is displayed on display 36. This identification is known as navigation or localization. An icon representing the localized point or instruments may be shown on the display 36 within several two-dimensional image planes, as well as on three and four dimensional images and models.

The navigation system 10 may be able to detect the position of the patient's anatomy and the position of the catheter 52 (e.g., the sensor coupled to the heart wall) or other surgical instrument, or data related thereto. Data related to the positions of these two items may be used to allow the navigation system 10 to compute and display the position of the catheter 52 in relation to the patient 14. The tracking system 44 is employed to track the catheter 52 and the anatomy simultaneously.

The tracking system 44 essentially works by positioning the transmitter coil array 46 adjacent to the patient space to generate a low-energy magnetic field generally referred to as a navigation field. Because every point in the navigation field or patient space is associated with a unique field strength, the electromagnetic tracking system 44 can determine the position of the catheter 52 by measuring the field strength at the sensor 58 location. The dynamic reference frame 54 is fixed to the patient 14 to identify the location of the patient in the navigation field. The electromagnetic tracking system 44 continuously recomputes the relative position of the dynamic reference frame 54 and the catheter 52 during localization and relates this spatial information to patient registration data to enable image guidance of the catheter 52 within the patient 14, or tracking of the sensor to provide wall motion.

Patient registration is the process of determining how to correlate the position of the instrument or catheter 52 on the patient 14 to the position on the diagnostic or pre-acquired images. To register the patient 14, the physician or user will select and store particular points from the pre-acquired images and then may touch the corresponding points on the patient's anatomy with a pointer probe 66. The navigation system 10 analyzes the relationship between the two sets of points that are selected and computes a match, which correlates every point in the image data with its corresponding point on the patient's anatomy or the patient space. The points that are selected to perform registration are the fiducial arrays or landmarks 60. Again, the landmarks or fiducial points 60 are identifiable on the images and identifiable and accessible on the patient 14 (e.g., a patient's heart). For example, the landmarks 60 can be artificial landmarks 60 that are positioned on the patient 14, can be reference landmarks on or in the heart (e.g., a catheter looped in a heart chamber or a catheter in the percardial space), or can be any other suitable landmarks such as, for example, anatomical landmarks that can be easily identified in the image data. The system 10 may also perform 2D to 3D registration by utilizing the acquired 2D images to register 3D volume images by use of contour algorithms, point algorithms or density comparison algorithms.

According to one or more embodiments described herein, a system, like that of system 10, or similar to that of system 10, includes at least one pair of electromagnetic sensor coils utilized not only in a navigational capacity, as described in U.S. Patent Application Publication No. 2004/0097806, but also in a monitoring capacity for use in selecting one or more cardiac pacing sites intra-operatively, that is, at a time of pacing electrode implant (e.g., such as in monitoring heart wall motion for use in selecting one or more pacing sites).

Figure 2A:
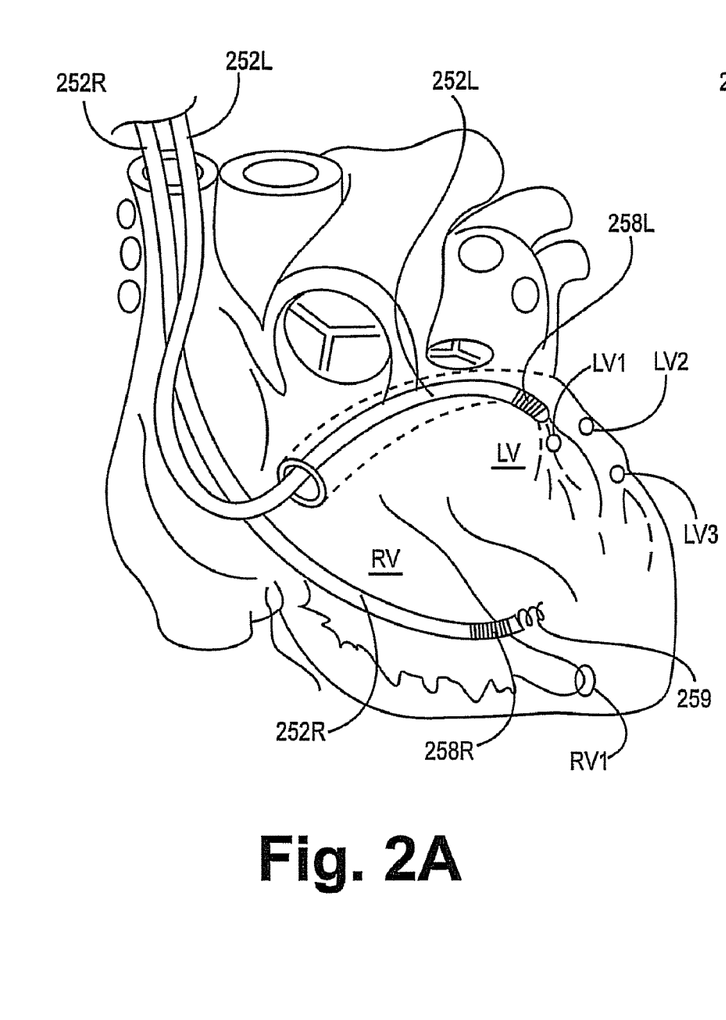
FIGS. 2A-2C are schematics showing various cardiac monitoring and pacing sites according to one or more exemplary methods of the present disclosure.
Figure 2B:
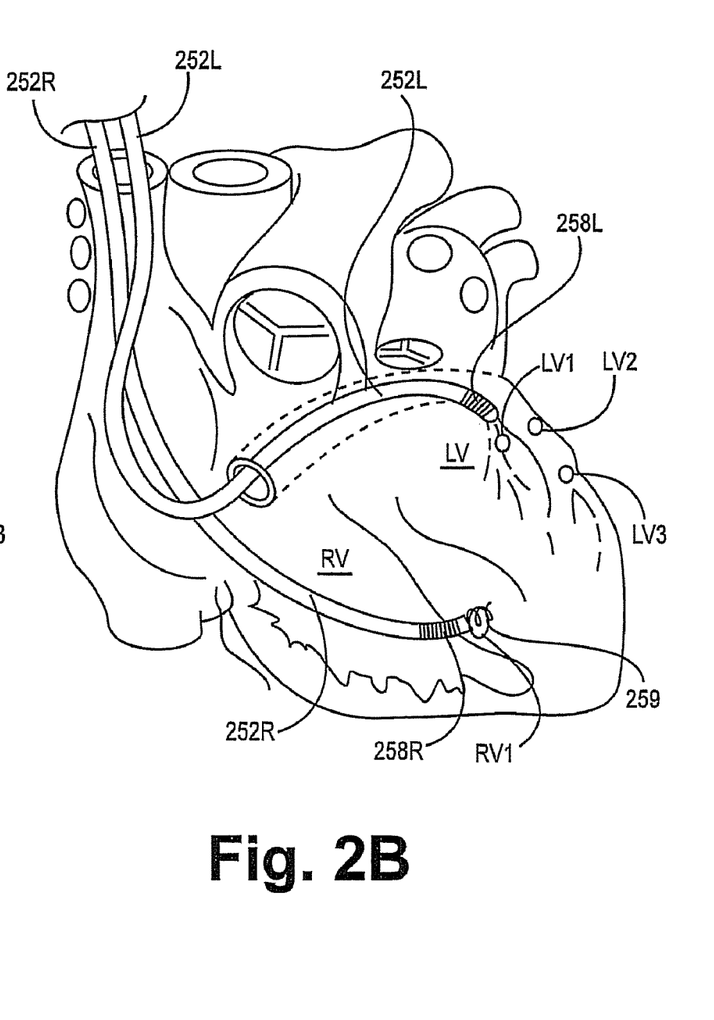
Figure 2C:
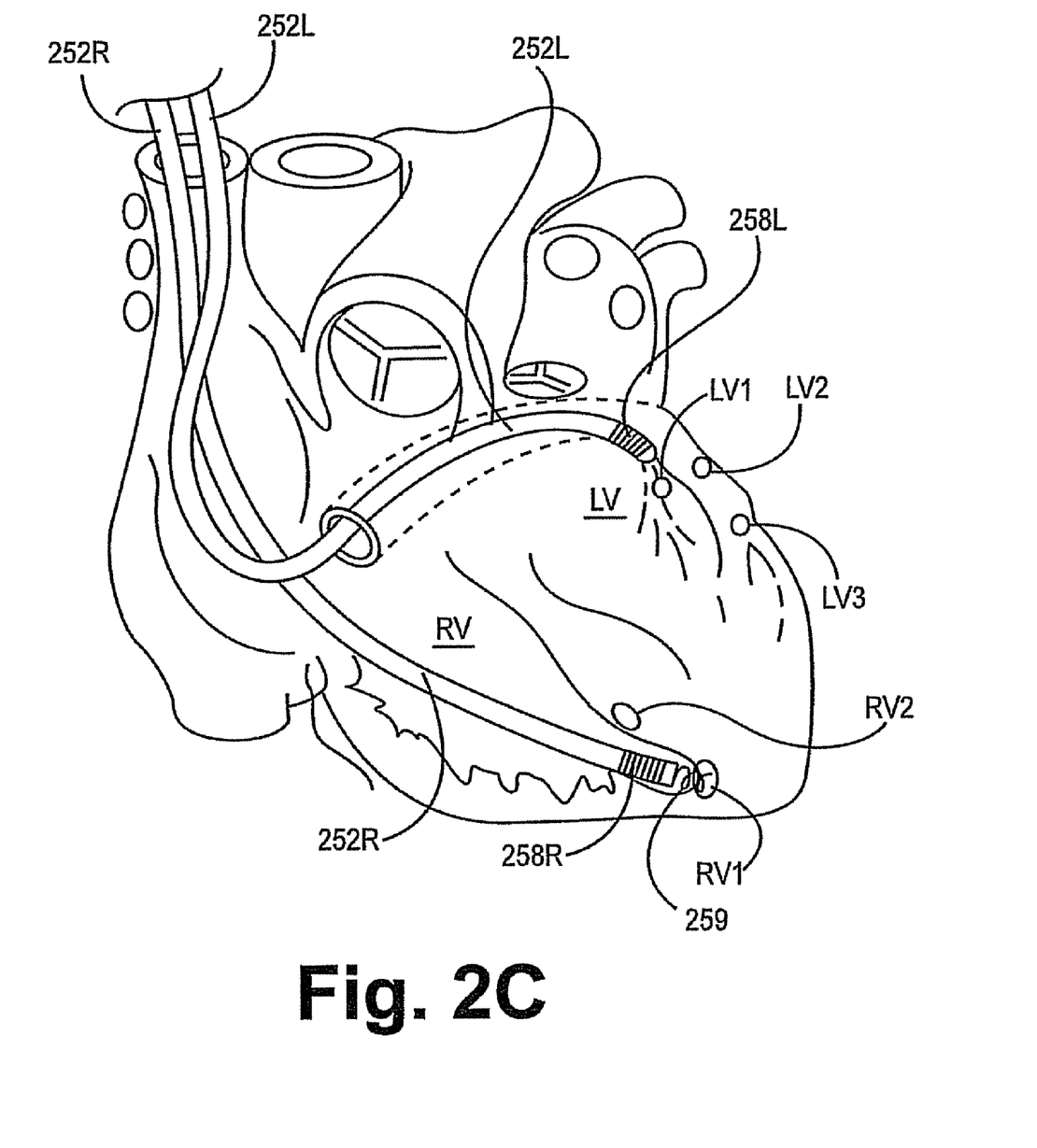

FIGS. 2A-2C are schematics showing various cardiac monitoring and pacing sites according to one or more embodiments of the present disclosure. FIGS. 2A-2C illustrate a first elongate lead 252R extending into a right ventricle (RV) and a second elongate lead 252L extending into a coronary vein over a surface of a left ventricle (LV); each of leads 252R and 252L include an electromagnetic sensor coil 258R, 258L, respectively, which has been positioned to monitor cardiac wall motion. Voltage signals from coils 258L, 258R, which are generated by a current induced therein by an external magnetic field, for example, created by coil array controller 48 driving coils in array 46 (FIG. 1), facilitate creation of a virtual representation of leads 252R, 252L, respectively, in proximity to the RV and LV walls, and thereby provide RV and LV heart wall motion data (e.g., as a result of tracking the sensor coil within the patient during a cardiac cycle as the heart wall moves).

As described herein, the term 'lead' is employed herein in a generic sense to denote a body carrying at least one sensor (e.g., a sensor coil) and an associated lead wire (unless wireless communication is used); as such, either or both of leads 252R and 252L may further be adapted to carry out additional functions, for example, in facilitating delivery of pacing to a target site, and can, thus, in various embodiments, take the form of a guidewire, a catheter, a pacing lead, a delivery device, etc.). It should be noted that the voltage signals from each of coils 258R, 258L may be used for image guided navigation of leads 252R and 252L, respectively, to the illustrated positions, for example, according to methods described in U.S. Patent Application Publication No. 2004/0097806. Furthermore, it should be noted, that each of leads 252R, 252L may include a plurality of sensor coils spaced apart from one another along a length thereof, to provide more enhanced wall motion data.

Figure 3:
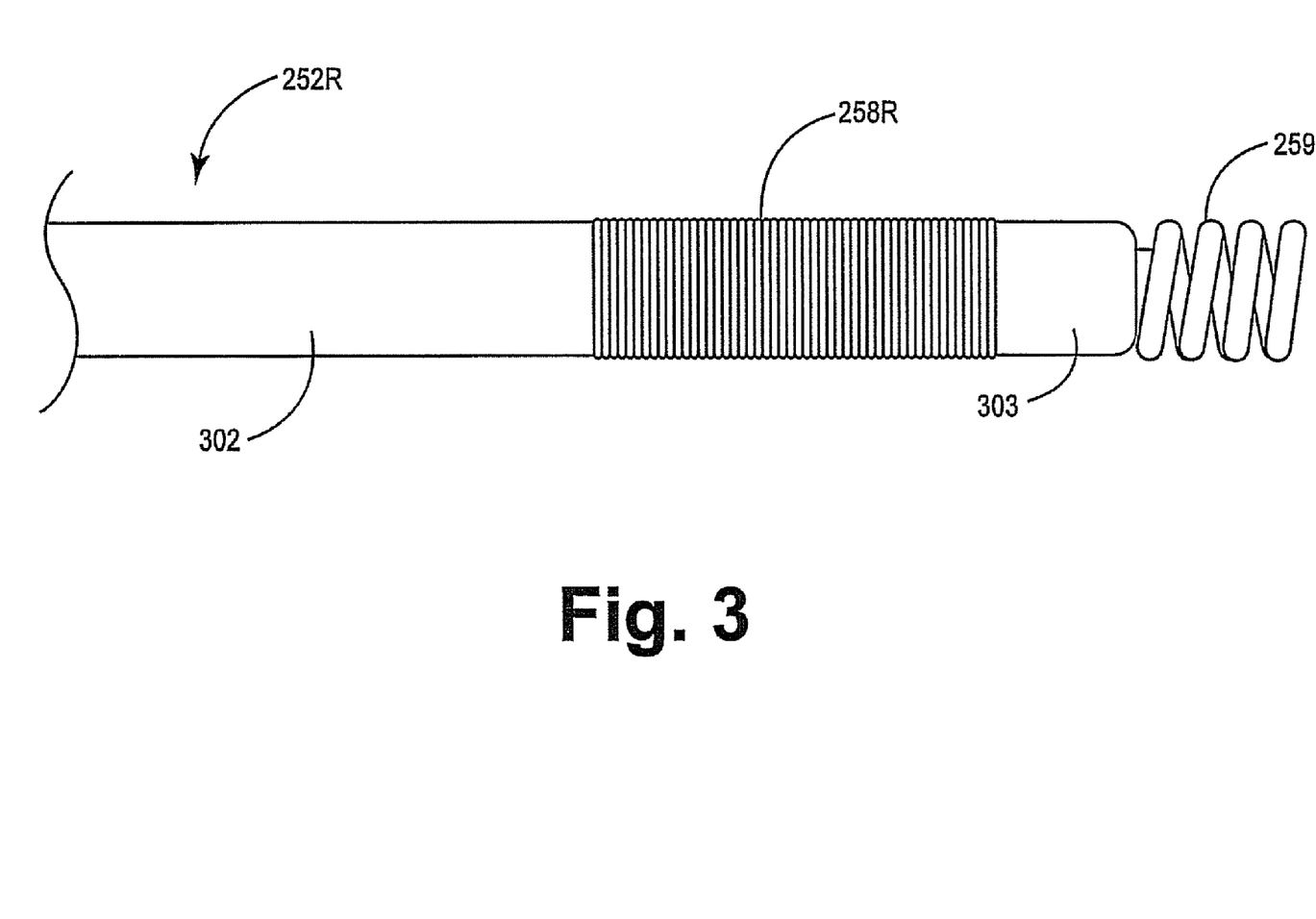
FIG. 3 is a plan view of a distal portion of a lead employed in carrying out one or more exemplary methods of the present disclosure.

FIG. 3 is a plan view of a distal portion of lead 252R that may be used in one or more embodiments described herein. FIG. 3 illustrates a fixation element 259 terminating a distal segment 303 of lead 252R, coil 258R extending proximally from segment 303, and a body 302 of lead 252R extending proximally from coil 258R; element 259 serves to secure coil 258R at a position along a heart wall. According to one or more embodiments of the present disclosure, segment 303 is relatively rigid, for example, being formed from a 75D durometer polyurethane, so that coil 258R will move in sync with that portion of the heart wall to which element 259 is fixed, while body 302 is relatively supple, or flexible, for example, being formed predominately from silicone rubber, so as not to influence the response of coil 258R to the wall motion. At least in one or more embodiments, lead wires for coil 258R extend proximally therefrom, within body 302 to couple, for example, with probe interface 50 (FIG. 1). An exemplary assembly for coil 258R (as well as for coil 258L), which may be incorporated by one or more embodiments of the present disclosure, is described in conjunction with FIGS. 3A-C of commonly assigned and co-pending patent application entitled THERAPY DELIVERY SYSTEM INCLUDING A NAVIGATION ELEMENT and having the U.S. patent application Ser. No. 11/322,393, and the FIGS. 3A-C, along with the associated description, of this application are hereby incorporated by reference.

It should be noted that, in the context of the present disclosure, fixation of a sensor (e.g., a sensor or receiver coil), for example, coil 258L, to a heart wall can encompass fixation to a coronary vein. Furthermore, it should be noted that one or more embodiments of methods or systems described herein may use other types of suitable sensors, and also may use, for example, leadless, or wireless, electromagnetic sensor coils, an example of which is described in co-pending and commonly-assigned U.S. patent application Ser. No. 11/565,283, which is hereby incorporated by reference in its entirety.

With reference back to FIGS. 2A-2B, according to some methods of the present disclosure, coil 258R is fixed, or secured, at a position along the RV septal wall by fixation element 259 of lead 252R, and coil 258L may be secured along the LV wall by lodging a distal tip of lead 252L deep within the coronary vein. It should be noted that lead 252L may also include a fixation element to secure coil 258R at a position along the LV wall, so that the secured position is not dependent upon an anatomy of the coronary vasculature. An alternate position for the fixation of coil 258R, which is in closer proximity to the RV apex, is shown in FIG. 2C. It should be noted that, although FIGS. 2A-2C illustrate transvenous approaches for positioning coils 258R, 258L, within the venous system, the disclosure is not so limited, and one or both of coils 258R, 258L may be fixed, or secured to an epicardial surface of the heart, for example, via a trans-thoracic or sub-xiphoid approach.

With further reference to FIGS. 2A-2C, non-paced heart wall motion data may be collected, or sampled, for example, from coils 258R, 258L for comparison with collected or sampled sets of paced heart wall motion data that result from pacing at an RV site RV1 (FIG. 2A) in combination with pacing at different LV sites LV1, LV2, LV3. Alternately, or additionally, sets of paced heart wall motion data that result from pacing at another RV site RV2 (FIG. 2B) in combination with pacing at the LV sites LV1, LV2, LV3 may be compared to the non-paced heart wall motion data. According to one exemplary method, heart wall motion data sets, for example, are averaged over multiple (e.g., five) heart beats, for the non-paced condition and each of the paced conditions that correspond to each pair of selected pacing sites, may be collected and stored for projection onto a pre-acquired image of the patient's heart, for example, a fluoroscopic image generated by imaging device 12 (FIG. 1). Each of these wall motion data sets, which are presented by the motion of the virtual representation of sensor coil 258R on the pre-acquired image, may then be viewed, for example, on display 36 of workstation 34 (FIG. 1), when a user 'clicks on', or selects via the interface 38 of workstation 34, landmarks in the pre-acquired image that have been associated with each of the selected pacing sites.

Although an electromagnetic tracking system may be used to provide heart wall motion data as described herein (e.g., sensing and tracking movement of an electromagnetic sensor coil during one or more paced or non-paced cardiac cycle), such heart wall motion data may be provided using one or more other types of navigation and/or tracking systems. For example, tracking and/or mapping systems that, for example, detect movement of electrodes in an electrical field (e.g., such as created by current injection on surface electrodes) by measuring voltage on the electrode with respect to a reference electrode, such as described in U.S. Pat. No. 5,697,377 entitled "Catheter Mapping System and Method" issued Dec. 16, 1997 and U.S. Pat. No. 5,983,126 entitled "Catheter Location System and Method" issued Nov. 9, 1999, may be used to provide heart wall motion data that may be visualized or used for any other purpose as described herein. Still further, for example, methods of evaluating motion of tissue using electrical field tomography, such as described in U.S. Patent Application Publication No. 2008/0058656 entitled "Electric Tomography," may be used to provide heart wall motion data that may be visualized or used for any other purpose as described herein. Yet still further, for example, optical components, such as in optical fiber sensing systems, such as described in U.S. Patent Application Publication No. 2008/0285909 entitled "Optical Fiber Shape Sensing Systems" may be used to provide heart wall motion data that may be visualized or used for any other purpose as described herein. As such, it will be recognized that various types of systems may be used to provide wall motion data to be process and visualized or used for any other purpose as described herein. Although data collected by one or more methods may be more advantageous than others (e.g., using the same system to collect wall motion data as navigating pacing leads to pacing sites may be advantageous).

Lead placement may be optimized for any number of pacing therapies based on wall motion data (e.g., acquired as described herein or in any other manner). In addition, optimization of A-V and/or V-V timing may be defined or selected in a like manner (e.g., a selection of pacing lead location and/or settings may be based on wall motion data). As such, processes using wall motion data to select pacing lead location could also be used to optimize the settings for performing such pacing using such pacing leads (e.g., pacer timing settings).

As described herein, various methods have been used to guide and detect a lead, such as a catheter probe, through the internal spaces of a patient undergoing a surgical procedure.

For example, also as described herein, the location data regarding such a catheter probe may be obtained from electrical measurements of voltage signals that are induced within a sensing coil affixed to the catheter probe (e.g., the distal end thereof. These induced voltage signals are generated by the sensing coil, at least in one or more embodiments, in response to prespecified electromagnetic fields that project into the anatomical region of interest which contains all prospective locations of the catheter probe. The electrical measurements of the induced signals provide sufficient information to compute the angular orientation and the positional coordinates of the sensing coil, and hence the catheter probe, which collectively define the location of the sensing coil. For example, the catheter probe may be positioned on the endocardial surface and/or epicardial surface, and used to measure wall motion (e.g., location of the sensing coil positioned on the wall) over one or more cardiac cycles. In other words, changes in wall motion may be measured at the site of the sensing coil affixed to the catheter probe (e.g., either when the heart is not being paced or while altering pacing locations within and/or outside the RV, LV, or both).

Optimization of cardiac mechanical activation during pacing lead placement may include selecting lead placement by maximizing the magnitude of wall motion and/or the timing of wall motion, the velocity of such wall motion, or the acceleration of such wall motion, such as during isovolumic contraction and/or relaxation, or such as during systole and/or diastole. Still further, for example, optimization of cardiac mechanical activation during acute pacing lead placement may include minimizing differences in wall motion magnitude and/or the timing of wall motion, the velocity of such wall motion, or the acceleration of such wall motion, such as during isovolumic contract and/or relaxation, or such as during systole and/or diastole.

Although not limited thereto, in one or more embodiments, the methods or systems use pre-programmed algorithms (e.g., executable and/or stored by workstation 34) to process wall motion data (e.g., wall motion data collected from coils 258R, 258L) to generate image data or any other type of notification information or data (e.g., data used to notify a user) that can assist a physician in selecting one or more effective pacing sites. For example, such image data may assist such selection by facilitating a methodical comparison between baseline non-paced mechanical function of the heart and the mechanical function thereof in response to pacing at one or more sites (e.g., bi-ventricular pacing). For example, such algorithms may be used to process wall motion data to generate plots comparing non-paced mechanical function of the heart and the mechanical function thereof in response to pacing at one or more sites, motion loop images comparing non-paced mechanical function of the heart and the mechanical function thereof in response to pacing at one or more sites, image data representative of the synchrony between paced wall motion data and non-paced wall motion data, and image data representative of the relative motion between apex and base of the heart in a non-paced and/or paced cardiac cycle.

In other words, real time data may be provided to a user to assist the user in selecting one or more pacing sites. For example, such data may be image data giving a visualization of heart wall motion data collected over one or more cardiac cycles or notification by the system that a pacing location is not desirable (e.g., such as when compared to another pacing site or a non-paced condition). For example, a user may be presented such image data on the display 36 or provided notification in another manner (e.g., visual notification, tactile notification, audible notification, etc.).

Further, in one or more embodiments, leads including sensors are positioned along each of the RV heart wall and the LV heart wall. The sensors are usable to track wall motion at their respective positions. A computer (e.g., a controller) is operable to receive heart wall motion data for one or more cardiac cycles when the heart is paced and/or when the heart is not paced. A computer program (e.g., including one or more instructions) is used to manipulate the data as desired to provide an output that assists a user in selection of a pacing site for one or more pacing electrodes.

For example, non-paced heart wall motion data may be compared to paced heart wall motion data to generate image data representative of such a comparison and indicative of the effectiveness of pacing at a pacing site. Likewise, paced heart wall motion data resulting from pacing at a first pacing site may be compared to paced heart wall motion data at one or more other pacing sites to generate image data representative of such a comparison and indicative of the effectiveness of pacing at one of such pacing sites. For example, the display 36 may be used visualize the image data representative of the comparison to assist a user in selecting a pacing site.

For example, image data representative of first and second motion loops may be generated corresponding to the motion of the heart wall during at least one non-paced cardiac cycle (e.g., heart wall motion loops in both the right and left ventricles) and image data may be generated representative of first and second motion loops corresponding to the motion of the heart wall during at least one paced cardiac cycle (e.g., heart wall motion loops in both the RV and LV). The display can then visualize such motion loops alone or in combination with a representation of the heart. Further, such heart wall motion loops (e.g., multiple data points forming trajectories representative of the wall motion during a cardiac cycle) may be compared over multiple cycles to generate image data representative of heart wall motion of the RV relative to heart wall motion of the LV for both paced and non-paced conditions (e.g., image data representative of distances between corresponding points of the motion loops may be generated).

Still further, image data may be generated such that a user may select a pacing site based on maximizing wall motion (or the derivable quantities thereof, such as velocity, acceleration, or strain), based on minimizing the difference between time to peak wall motion or velocity (e.g., synchronization characteristics), or based on a combination thereof. In other words, in one or more embodiments, a user may select a pacing site based on the timing of the wall motion data collected in either a non-paced or paced condition, and/or the magnitude of such wall motion (e.g., an optimal pacing site may correspond to a maximum difference in a voltage of the signal induced in the sensors relative to a reference voltage, such as, for example, ground).

Figure 4A:
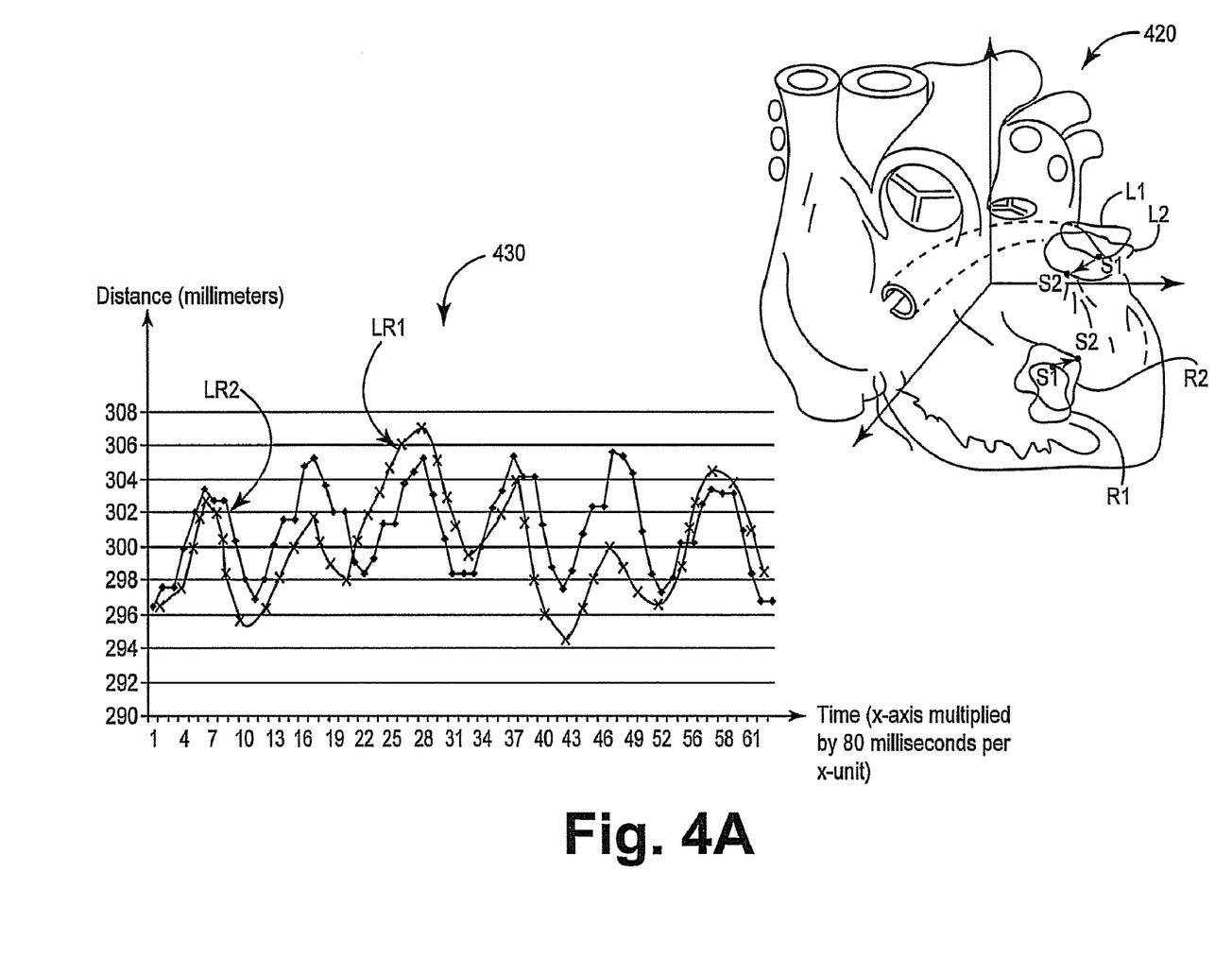
FIGS. 4A-4C are exemplary analysis images (e.g., plots) which may be generated with data collected using one or more exemplary methods and systems of the present disclosure.
Figure 4B:
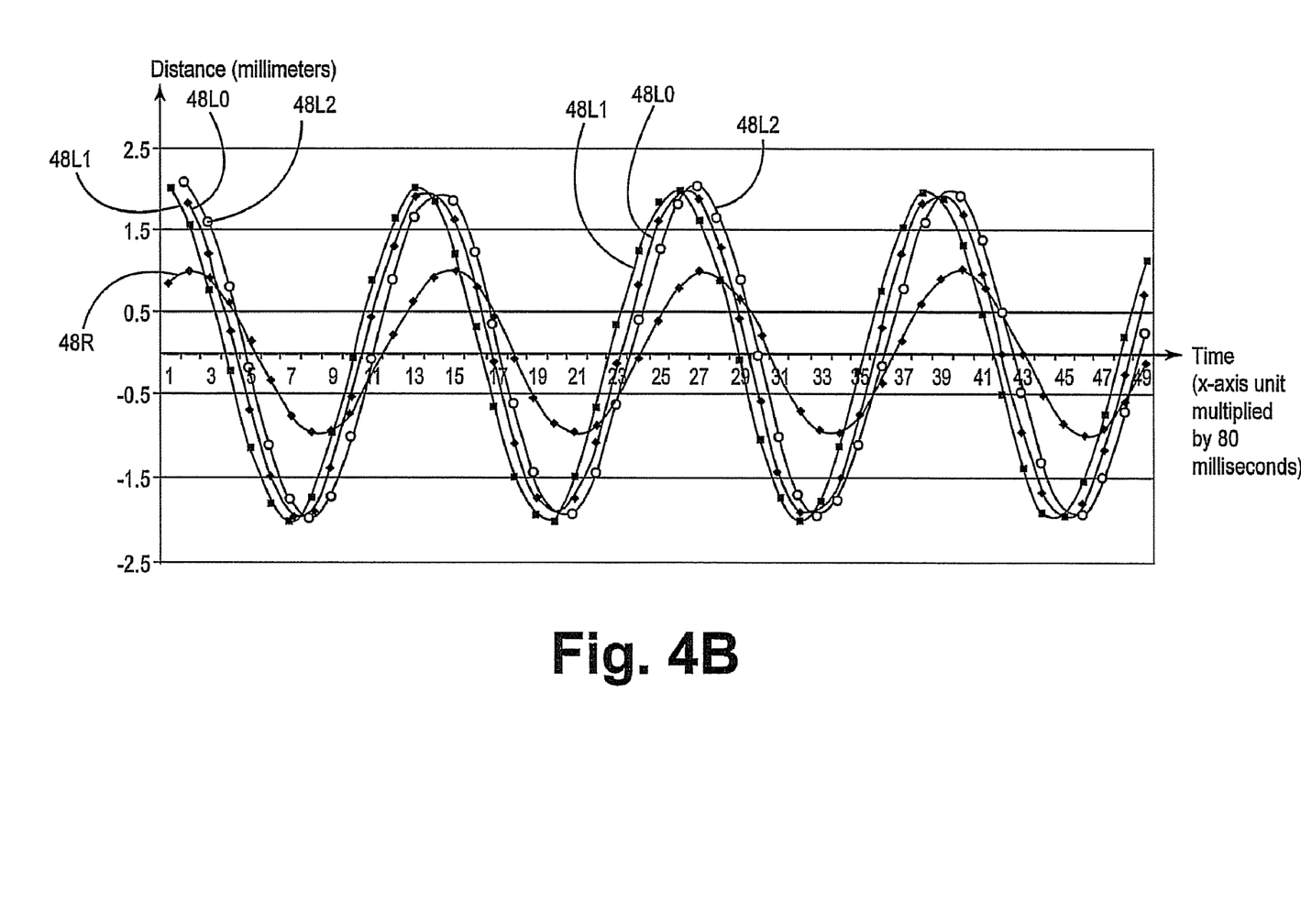
Figure 4C:
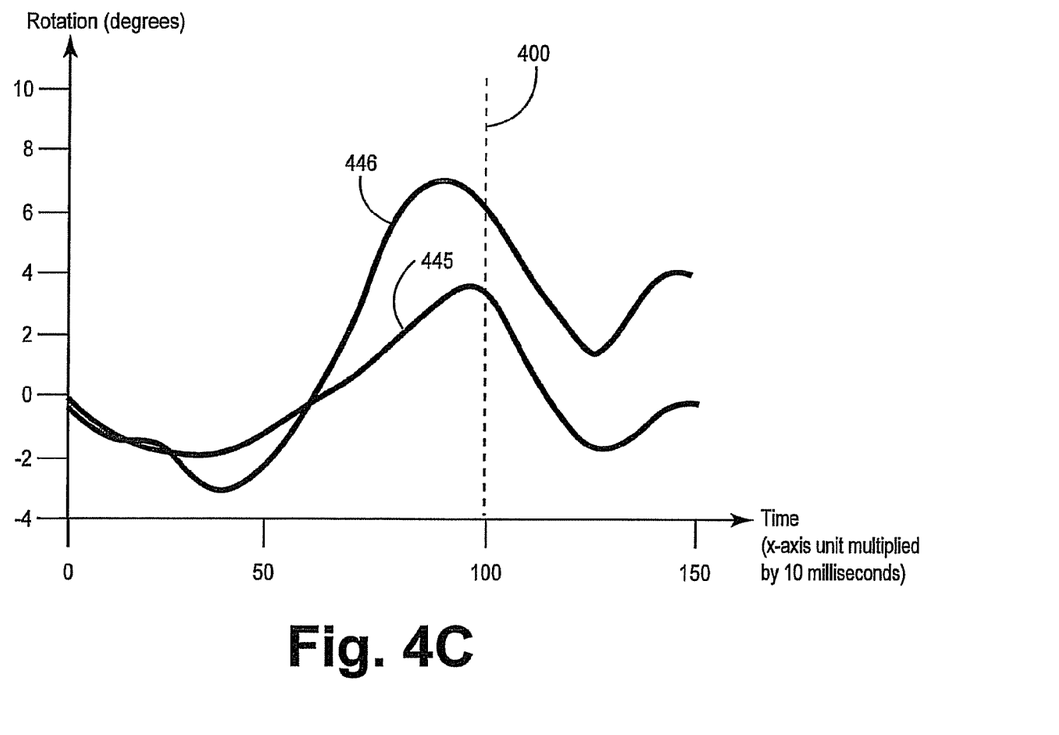

Various examples of using heart wall motion in the selection of pacing location are described herein in conjunction with FIGS. 4A-4C. For example, the visualization of heart wall motion to a user (e.g., collected during pacing and when the heart is not paced) provides the user with information of the effectiveness of the location of pacing at one or more pacing sites. Thus, the user is assisted in selecting a desirable pacing location.

FIG. 4A is an exemplary display including a 3D plot 420 of wall motion data, for example, averaged over six cycles, which is superimposed on an image of a patient's heart, and a 2D plot 430, of distances mapped between coils 258R, 258L, at particular points in time for each of the six cycles. The plotted wall motion data is not actual data, but is representative of data that could be collected from coils 258R, 258L. Plot 420 shows a first condition represented by a pair of simultaneous motion loops L1 and R1 created, for example, from averaged wall motion data collected from coils 258L and 258R, respectively, either when the heart is not paced, or when the heart is paced at at least one of pacing sites LV1, LV2, or LV3. For comparison, plot 420 also shows a second condition, represented by a pair of simultaneous motion loops L2 and R2 created, for example, from averaged wall motion data collected from coils 258L and 258R, for pacing that has been adjusted, either being applied (vs. no pacing), or being applied at a different site, from that which resulted in loops L1 and R1. Point S1 on each of loops L1 and R1 corresponds to an approximate position of the respective heart wall portion at systole for the first condition, and point S2 on each of loops L2, R2 to an approximate position of the respective heart wall portion at systole for the second condition. With reference to points S1, S2, it may be appreciated that motion loops L2, R2 show a greater contraction between the heart wall portions and a greater relative rotation therebetween, which is indicative of a twisting, or torsion, from apex to base, that will be described in greater detail below.

Plot 430 presents the first and second conditions in a different manner wherein a distance between corresponding points of each of the motion loops that have been averaged to create loops L1 and R1, are plotted over time for the six cycles for comparison with a distance between corresponding points of each of the motion loops that have been averaged to create loops L2 and R2. The six cycles may be identified by the six peak magnitudes for each curve. Distances between points of loop L1 and points of loop R1 make up curve LR1, and distances between points of loop L2 and points of loop R2 make up curve LR2. With reference to plot 430 it may be appreciated that the repeatability of magnitudes of the distances making up curve LR2 is greater than that for curve LR1 over the six cycles, which may be an indication of better synchrony between left and right heart wall motion. Thus, with reference to the display of FIG. 4A, one may determine that the pacing resulting in the second condition, represented by loops L2, R2 and curve LR2, provides a better hemodynamic response than the lack of pacing or pacing at another site resulting in the first condition, represented by loops L1, R1 and curve LR1. Other methods for comparing heart wall motion data will be discussed below, in conjunction with FIGS. 4B and 4C.

Pacing may be applied at the sites, either endocardial or epicardial, by pacing lead electrodes which have been delivered to the sites by a transvenous or a trans-thoracic or a sub-xiphoid approach, according to a variety of methods. According to one or more embodiments of the present disclosure, one or both of leads 252R, 252L further include an electrode for delivering the pacing stimulation; for example, in FIG. 2B fixation element 259 may double as a pacing electrode to deliver pacing stimulation at site RV2. According to methods of the present disclosure, wall motion data for any group of pacing sites may be iteratively collected for comparison with non-paced wall motion data, to select one or more preferred pacing sites.

The pacing sites shown are in areas generally corresponding to effective bi-ventricular pacing sites, but, it should be noted that methods and systems of the present disclosure are not limited to these particular pacing sites. In the context of bi-ventricular pacing for CRT, a difference between paced and non-paced heart wall motion is typically sought, since non-paced wall motion will be asynchronous and the objective is to achieve synchrony; however in a different context, for example, in selecting one or more pacing sites for bradycardia or tachyarrhythmia therapy, a similarity between paced and non-paced heart wall motion is sought, since the objective is to maintain the already synchronous heart wall motion.

According to one or more embodiments, the wall motion data corresponding to various pacing sites from secured RV and LV coils, for example, coils 258R and 258L, respectively, is processed and plotted to provide a picture of RV and LV wall motion with respect to one another, in the time domain. FIG. 4B is an exemplary plot of a net motion of 3D wall motion data. The plotted wall motion data is not actual data, but is representative of data that could be collected from coils 258R, 258L. With reference to FIG. 4B, in conjunction with FIG. 2A, a first curve 48R is generated from non-paced wall motion data collected from coil 258R, a second curve 48L0 is generated from non-paced wall motion data collected from coil 258L, a third curve 48L1 is generated from paced wall motion data collected from coil 258L, wherein pacing is applied at a first pair of sites, RV1 and LV1, and a fourth curve 48L2 is generated from paced wall motion data collected from coil 258L, wherein pacing is applied at a second pair of sites, RV1 and LV2. The plot of FIG. 4B indicates that pacing at sites RV1 and LV2, which results in the wall motion depicted by curve 48L2, brings LV heart wall motion closer into phase, or synchrony with RV heart wall motion, which is represented by first curve 48R.

According to one or more embodiments, pacing sites may be selected according to maximum cardiac wall motion, either RV, LV or both. According to an exemplary method of this type, the wall motion data from secured coils 258R, 258L, positioned as shown in FIG. 2C, is processed to generate a plot describing a differential rotation between an apex and a base of the heart. Alternately, for example, wall motion data from a plurality of sensor coils disposed along a length of lead 252R positioned in the RV as shown in FIG. 2C and from a plurality of sensor coils disposed along a length of lead 252L positioned in the cardiac vein, as shown in FIG. 2C, can provide more detailed information concerning the differential rotation. This differential rotation is indicative of the characteristic twisting or torsion, from apex to base, of cardiac contraction; the twisting is commonly described as a wringing-out motion that 'squeezes' the blood out from the RV and LV during systole. The effectiveness of the motion is often measured in terms of an ejection fraction, that is, a ratio of the blood that is ejected from the LV to that which is contained in the LV at the peak of filling, or diastole.

FIG. 4C is a plot of relative rotation (ordinate) between apex and base, in terms of degrees, versus time (abscissa), in terms of percent of systole, which may be generated from a torsion analysis of the wall motion data for a paced and an un-paced condition. Dashed line 400 corresponds to a closing of the aortic valve at 100% systole. A first curve 445 of the plot is indicative of a relatively low ejection fraction, and may correspond to an un-paced condition, while a second curve 446 is indicative of a more normal ejection fraction, wherein the relative rotation between apex and base has been increased, for example, via pacing. One or more additional pacing sites may be tested, and the corresponding sets of wall motion data collected and plotted, per FIG. 4C, to find out if an even greater relative rotation can be induced. According to another exemplary method, wall motion indicative of ejection fraction may be observed in terms of short and/or long axis contraction and expansion for the LV.

With reference back to FIG. 1, as described herein, pre-programmed algorithms of workstation 34 may process wall motion data collected from coils 258R, 258L to generate plots or other image data, for example, like those described above in conjunction with FIGS. 4A-4C. Such plots, or other image data, for example, displayed on display 36 of workstation 34, can help a physician to select one or more effective pacing sites by facilitating a methodical comparison between baseline non-paced mechanical function of the heart and the mechanical function thereof in response to pacing at various sites.

In the foregoing detailed description, the disclosure has been described with reference to specific embodiments. However, it may be appreciated that various modifications and changes can be made without departing from the scope of the disclosure as set forth in the appended claims.

We claim:

1. A system for use in selecting at least one cardiac pacing site, the system comprising:
   a first elongate lead configured to be positioned along a right ventricular heart wall, wherein the first elongate lead comprises a first electromagnetic sensor in which a first signal is induced when positioned in a magnetic field, wherein the first signal is usable to track wall motion when the first elongate lead is directed to a first position along the right ventricular heart wall;
   a second elongate lead configured to be positioned along a left ventricular heart wall, wherein the second elongate lead comprises a second electromagnetic sensor in which a second signal is induced when positioned in a magnetic field, wherein the second signal is usable to track wall motion when the second elongate lead is directed to a second position along the left ventricular heart wall;
   a controller configured to receive non-paced heart wall motion data based on signals induced in each of the first and second electromagnetic sensors when the first and second electromagnetic sensors are secured at the corresponding first and second positions, wherein the controller is further configured to receive paced heart wall motion data based on signals induced in each of the first and second electromagnetic sensors when the first and second electromagnetic sensors are secured at the corresponding first and second positions and cardiac pacing stimulation is applied at one or more first pacing sites, and further wherein the controller is configured to execute a program to generate image data representative of a comparison of non-paced heart wall motion and paced heart wall motion based on at least a portion of the non-paced heart wall motion data and at least a portion of the paced heart wall motion data, wherein the image data representative of the comparison is indicative of the effectiveness of pacing at the one or more first pacing sites; and
   a display to visualize the image data representative of the comparison to assist a user in selecting at least one pacing site.

2. The system of claim 1, wherein the controller is configured to receive non-paced heart wall motion data comprising non-paced motion loop data representative of heart wall motion during at least one non-paced cardiac cycle collected based on signals induced in each of the first and second electromagnetic sensors when the first and second electromagnetic sensors are secured at the corresponding first and second positions,
   wherein the controller is further configured to receive paced heart wall motion data comprising paced motion loop data representative of heart wall motion during at least one paced cardiac cycle collected based on signals induced in each of the first and second electromagnetic sensors when the first and second electromagnetic sensors are secured at the corresponding first and second positions and cardiac pacing stimulation is applied at the one or more first pacing sites,
   and further wherein the controller is configured to execute a program to generate image data representative of first and second motion loops corresponding to the motion of the heart wall during the at least one non-paced cardiac cycle based on the non-paced motion loop data and to generate image data representative of first and second motion loops corresponding to the motion of the heart wall during the at least one paced cardiac cycle based on the paced motion loop data, wherein the display is operable to visualize the image data representative of first and second motion loops corresponding to the motion of the heart wall during the at least one non-paced cardiac cycle and the image data representative of first and second motion loops corresponding to the motion of the heart wall during the at least one paced cardiac cycle.

3. The system of claim 2, wherein the image data comprises data for displaying a first and second loop corresponding to the motion of the heart wall during the at least one non-paced cardiac cycle, wherein the image data comprises data for displaying a first and second loop corresponding to the motion of the heart wall during the at least one paced cardiac cycle, and further wherein the display is operable to display the first and second loop corresponding to the motion of the heart wall during the at least one non-paced cardiac cycle and the first and second loop corresponding to the motion of the heart wall during the at least one paced cardiac cycle relative to a representation of the heart.

4. The system of claim 1, wherein the controller is configured to receive non-paced heart wall motion data comprising non-paced motion loop data representative of heart wall motion during multiple non-paced cardiac cycles collected based on signals induced in each of the first and second electromagnetic sensors when the first and second electromagnetic sensors are secured at the corresponding first and second positions, wherein the controller is further configured to receive paced heart wall motion data comprising paced motion loop data representative of heart wall motion during multiple paced cardiac cycles collected based on signals induced in each of the first and second electromagnetic sensors when the first and second electromagnetic sensors are secured at the corresponding first and second positions and cardiac pacing stimulation is applied at the one or more first pacing sites,
   and further wherein the controller is configured to execute a program associated therewith to:
   generate non-paced motion loop data representative of first and second motion loops corresponding to the motion of the heart wall at the respective first and second positions during each of the multiple non-paced cardiac cycles based on the non-paced motion loop data;
   generate paced motion loop data representative of first and second motion loops corresponding to the motion of the heart wall at the respective first and second positions during each of the multiple paced cardiac cycles based on the paced motion loop data;
   generate non-paced image data representative of a comparison of heart wall motion at the respective first and second positions for each of the multiple non-paced cardiac cycles based on the non-paced motion loop data;
   generate paced image data representative of a comparison of heart wall motion at the respective first and second positions for each of the multiple paced cardiac cycles based on the paced motion loop data, wherein the display is operable to visualize the non-paced and paced image data for each of the multiple cardiac cycles.

5. The system of claim 4, wherein the controller is configured to execute a program to generate non-paced image data representative of distances between corresponding points of the first motion loop relative to the second motion loop for each of the multiple non-paced cardiac cycles based on the non-paced motion loop data and to generate paced image data representative of distances between corresponding points of the first motion loop relative to the second motion loop for each of the multiple paced cardiac cycles based on the paced motion loop data.

6. The system of claim 1, wherein the controller is configured to receive non-paced heart wall motion data comprising non-paced wall motion data representative of heart wall motion during multiple non-paced cardiac cycles collected based on signals induced in each of the first and second electromagnetic sensors when the first and second electromagnetic sensors are secured at the corresponding first and second positions, wherein the controller is further configured to receive paced heart wall motion data comprising paced wall motion data representative of heart wall motion during multiple paced cardiac cycles collected based on signals induced in each of the first and second electromagnetic sensors when the first and second electromagnetic sensors are secured at the corresponding first and second positions and cardiac pacing stimulation is applied at the one or more first pacing sites, and further wherein the controller is configured to execute a program to generate image data representative of the difference in phase of heart wall motion at the first and second positions in the time domain based on the non-paced wall motion data and the paced wall motion data for each of the multiple cardiac cycles.

7. The system of claim 1, wherein the controller is configured to receive non-paced heart wall motion data comprising non-paced wall motion data representative of heart wall motion during at least one non-paced cardiac cycle collected based on signals induced in each of the first and second electromagnetic sensors when the first and second electromagnetic sensors are secured at the corresponding first and second positions, wherein the controller is further configured to receive paced heart wall motion data comprising paced wall motion data representative of heart wall motion during at least one paced cardiac cycle collected based on signals induced in each of the first and second electromagnetic sensors when the first and second electromagnetic sensors are secured at the corresponding first and second positions and cardiac pacing stimulation is applied at the one or more first pacing sites, and further wherein the controller is configured to execute a program to generate image data representative of the relative rotation of the heart from apex to base based on the non-paced wall motion data and the paced wall motion data.

8. The system of claim 1, wherein the controller is configured to execute a program to perform time domain analysis to determine a degree of synchrony between the wall motion at the position along the right ventricle and the wall motion at the position along the left ventricle based on at least a portion of the non-paced heart wall motion data and at least a portion of the paced heart wall motion data.

9. The system of claim 1, wherein the controller is configured to execute a program to perform torsional analysis to determine a relative rotation between the position along the right ventricular wall and the position along the left ventricular wall based on at least a portion of the non-paced heart wall motion data and at least a portion of the paced heart wall motion data.

10. A non-transitory computer-readable medium having stored thereon at least one instruction that, when executed by a computer, causes the computer to:

receive non-paced heart wall motion data representative of the motion of first and second sensors of first and second elongate leads secured at corresponding first and second positions along a right ventricular heart wall and a left ventricular heart wall, respectively;

receive paced heart wall motion data representative of the motion of the first and second sensors secured at the first and second positions along the right ventricular heart wall and the left ventricular heart wall, respectively, when cardiac pacing stimulation is applied at one or more first pacing sites;

generate data representative of a comparison of non-paced heart wall motion and paced heart wall motion based on at least a portion of the non-paced heart wall motion data and at least a portion of the paced heart wall motion data, wherein the image data representative of the comparison is indicative of the effectiveness of pacing at the one or more first pacing sites; and generate notification data indicative of the one or more first pacing sites being one of an optimal pacing site and a non-optimal pacing site.

11. The computer-readable medium of claim 10, having stored thereon at least one instruction that, when executed by the computer, causes the computer to:

generate image data representative of a comparison of non-paced heart wall motion and paced heart wall motion based on at least a portion of the non-paced heart wall motion data and at least a portion of the paced heart wall motion data, wherein the image data representative of the comparison is indicative of the effectiveness of pacing at the one or more first pacing sites; and visualize the image data representative of the comparison to assist a user in selecting at least one pacing site.

12. The computer-readable medium of claim 10, having stored thereon at least one instruction that, when executed by the computer, causes the computer to:

output image data for display to assist a user in introducing the first elongate lead to the first position along the right ventricular heart wall, the first elongate lead comprising a first electromagnetic receiver coil;

output image data for display to assist a user in coupling the first electromagnetic receiver coil at the first position along the right ventricular heart wall;

induce a first signal in the first electromagnetic receiver coil by generating a magnetic field, the first signal facilitating creation of a first virtual representation of at least a portion of the first elongate lead to direct the first elongate lead to the first position, and to track wall motion along the right ventricular heart wall;

output image data for display to assist a user in introducing the second elongate lead to the second position along a left ventricular heart wall, the second elongate lead comprising a second electromagnetic receiver coil;

output image data for display to assist a user in coupling the second electromagnetic receiver coil at the second position along the left ventricular heart wall;

induce a second signal in the second electromagnetic receiver coil by generating a magnetic field, the second signal facilitating creation of a second virtual representation of a portion of the second elongate lead to direct the second elongate lead to the second position, and to track wall motion along the left ventricular heart wall;

store a set of non-paced heart wall motion data from the signal of each of the electromagnetic receiver coils secured at the corresponding position;

apply cardiac pacing stimulation at the one or more first pacing sites;

collect a set of paced heart wall motion data from the signal of each of the electromagnetic receiver coils secured at the corresponding position;

compare the set of non-paced heart wall motion data to the set of paced heart wall motion data; and determine, based on the comparison, whether to maintain pacing at the one or more first pacing sites or to apply pacing stimulation at one or more second pacing sites for use in collection of a second set of paced heart wall motion data.

13. The computer-readable medium of claim 10, having stored thereon at least one instruction that, when executed by the computer, causes the computer to perform time domain analysis to determine a degree of synchrony between the wall motion at the position along the right ventricle and the wall motion at the position along the left ventricle based on at least a portion of the non-paced heart wall motion data and at least a portion of the paced heart wall motion data.

14. The computer-readable medium of claim 10, having stored thereon at least one instruction that, when executed by the computer, causes the computer to perform torsional analysis to determine a relative rotation between the first position along the right ventricular wall and the second position along the left ventricular wall based on at least a portion of the non-paced heart wall motion data and at least a portion of the paced heart wall motion data.

15. A method for use in selecting at least one cardiac pacing site, the method comprising:
 introducing a first elongate lead to a position along a right ventricular heart wall, the first elongate lead including a first electromagnetic receiver coil;
 coupling the first electromagnetic receiver coil at a first position along the right ventricular heart wall;
 inducing a first signal in the first electromagnetic receiver coil by generating a magnetic field, the first signal facilitating creation of a first virtual representation of at least a portion of the first elongate lead to direct the first elongate lead to the first position, and to track wall motion along the right ventricular heart wall;
 introducing a second elongate lead to a second position along a left ventricular heart wall, the second elongate lead including a second electromagnetic receiver coil;
 coupling the second electromagnetic receiver coil at the second position along the left ventricular heart wall;
 inducing a second signal in the second electromagnetic receiver coil by generating a magnetic field, the second signal facilitating creation of a second virtual representation of at least a portion of the second elongate lead to direct the second elongate lead to the second position, and to track wall motion along the left ventricular heart wall;
 storing a set of non-paced heart wall motion data from the signal of each of the electromagnetic receiver coils secured at the corresponding position;
 applying cardiac pacing stimulation at one or more first pacing sites;
 collecting a set of paced heart wall motion data from the signal of each of the electromagnetic receiver coils secured at the corresponding position;
 comparing the set of non-paced heart wall motion data to the set of paced heart wall motion data;
 determining, based on the comparison, whether to maintain pacing at the one or more first pacing sites or to apply pacing stimulation at one or more second pacing sites for collection of a second set of paced heart wall motion data;
 generating notification data indicative of the one or more first pacing sites being one of an optimal pacing site and a non-optimal pacing site.

16. The method of claim 15, wherein the first position along the right ventricular heart wall comprises a septal position.

17. The method of claim 15, wherein the first position along the right ventricular heart wall comprises a position located in proximity to an apex of the heart, and further wherein the second position along the left ventricular heart wall comprises a position in proximity to a base of the heart.

18. The method of claim 15, wherein comparing the set of non-paced heart wall motion data to the set of paced heart wall motion data comprises performing a time domain analysis to determine a degree of synchrony between the wall motion at the position along the right ventricle and the wall motion at the position along the left ventricle.

19. The method of claim 15, wherein comparing the set of non-paced heart wall motion data to the set of paced heart wall motion data comprises performing a torsional analysis to determine a relative rotation between the position along the right ventricular wall and the position along the left ventricular wall.

20. The method of claim 15, wherein the one or more first cardiac pacing sites comprise a left ventricular pacing site and a right ventricular pacing site.

21. The method of claim 20, wherein the first elongate lead further includes an electrode employed for applying the pacing stimulation to the right ventricular pacing site.

22. The method of claim 20, wherein the second elongate lead further includes an electrode employed for applying the pacing stimulation to the left ventricular pacing site.

23. The method of claim 15, further comprising:
 applying cardiac pacing stimulation at one or more second cardiac pacing sites;
 collecting a second set of paced heart wall motion data from the signal of each of the electromagnetic receiver coils secured at the corresponding position;
 comparing the set of non-paced heart wall motion data to the second set of paced heart wall motion data; and
 determining, based on the comparison, whether to maintain pacing at the one or more first pacing sites, or the one or more second pacing sites, or to apply pacing stimulation at one or more third pacing sites for collection of a third set of paced heart wall motion data.

24. A method for use in selecting at least one cardiac pacing site, the method comprising:
 coupling a first sensor at a first position along a right ventricular heart wall, the first sensor configured to track wall motion of the heart wall;
 coupling a second sensor at a second position along a left ventricular heart wall, the second sensor configured to track motion of the heart wall,
 collecting non-paced heart wall motion data based on the location of the first and second sensor at the corresponding positions;
 applying cardiac pacing stimulation at one or more first pacing sites;

collecting paced heart wall motion data based on the location of the first and second sensor at the corresponding positions when the cardiac pacing stimulation is applied;

comparing the non-paced heart wall motion data to the paced heart wall motion data;

generating image data, using an imaging device, representative of the comparison of non-paced heart wall motion data and paced heart wall motion data, wherein the image data representative of the comparison is indicative of the effectiveness of pacing at the one or more first pacing sites; and visualizing the image data representative of the comparison to assist a user in selecting a pacing site.

25. The method of claim 24, wherein the first position comprises a position located along a right ventricular septum.

26. The method of claim 24, wherein the first and second positions comprise positions located in proximity to an apex of the heart and located in proximity to a base of the heart, respectively.

27. The method of claim 24, wherein comparing the non-paced heart wall motion data to the paced heart wall motion data comprises performing a time domain analysis to determine a degree of synchrony between the wall motion at the first position and the wall motion at the second position.

28. The method of claim 24, wherein comparing the non-paced heart wall motion data to the paced heart wall motion data comprises performing a torsional analysis to determine a relative rotation between the first position and the second position.

29. The method of claim 24, wherein the one or more first pacing sites comprise a left ventricular pacing site and a right ventricular pacing site.

30. The method of claim 24, further comprising:

applying cardiac pacing stimulation at one or more second pacing sites;

collecting paced heart wall motion data based on the location of the sensors secured at the corresponding positions when the cardiac pacing stimulation is applied at the one or more second pacing sites;

comparing the non-paced heart wall motion data to the paced heart wall motion data collected when the cardiac pacing stimulation was applied at the one or more second pacing sites; and determining, based on the comparison, whether to maintain pacing at the one or more first pacing sites, or at the one or more second pacing sites, or to apply pacing stimulation at one or more third pacing sites for collection of additional paced heart wall motion data.

* * * * *